US005941874A

United States Patent [19]
Hohla

[11] Patent Number: 5,941,874
[45] Date of Patent: Aug. 24, 1999

[54] SIMULATING A LASER TREATMENT ON THE EYE BY PRETREATING A CONTACT LENS

[75] Inventor: Kristian Hohla, Vaterstetten, Germany

[73] Assignee: Chiron Technolas GmbH Opthalmologische Systeme, Munich, Germany

[21] Appl. No.: 08/814,435

[22] Filed: Mar. 10, 1997

[51] Int. Cl.[6] .......... A61N 5/06

[52] U.S. Cl. .......... 606/5; 606/2; 606/3; 606/10; 128/898

[58] Field of Search .......... 606/213–18; 128/898

[56] References Cited

U.S. PATENT DOCUMENTS 4,554,917 11/1985 Tagnon .
4,665,913 5/1987 L'Esperance, Jr. .
4,669,466 6/1987 L'Esperance .
4,721,379 1/1988 L'Esperance .
4,729,372 3/1988 L'Esperance, Jr. .
4,732,148 3/1988 L'Esperance, Jr. .
4,840,175 6/1989 Peyman .
4,856,513 8/1989 Muller .
4,881,808 11/1989 Bille et al. .
4,901,718 2/1990 Bille et al. .
4,902,122 2/1990 Azema et al. .
4,902,123 2/1990 Yoder, Jr. .
4,911,711 3/1990 Telfair et al. .
4,923,467 5/1990 Thompson .
4,941,093 7/1990 Marshall et al. .
4,973,330 11/1990 Azema et al. .
4,993,826 2/1991 Yoder, Jr. .
4,994,058 2/1991 Raven et al. .
4,998,819 3/1991 Labinger et al. .
5,098,426 3/1992 Sklar et al. .
5,106,183 4/1992 Yoder, Jr. .
5,137,530 8/1992 Sand .
5,147,352 9/1992 Azema et al. .
5,240,553 8/1993 Jones .
5,261,822 11/1993 Hall et al. .
5,279,611 1/1994 McDonnell .
5,295,989 3/1994 Nakamura .
5,374,265 12/1994 Sand .
5,404,884 4/1995 Lempert .
5,460,627 10/1995 O'Donnell, Jr. .......... 606/2
5,548,352 8/1996 Dewey .
5,591,185 1/1997 Kilmer et al. .......... 606/166

FOREIGN PATENT DOCUMENTS 111060 9/1983 European Pat. Off. .
151869 11/1984 European Pat. Off. .
207648 6/1985 European Pat. Off. .
191688 1/1986 European Pat. Off. .
224322 9/1986 European Pat. Off. .
209992 1/1987 European Pat. Off. .
WO 87 01930 4/1987 European Pat. Off. .
257836 7/1987 European Pat. Off. .
274205 11/1987 European Pat. Off. .
247260 3/1988 European Pat. Off. .
299836 6/1988 European Pat. Off. .
346116 6/1989 European Pat. Off. .
503802 9/1992 European Pat. Off. .
628298 5/1994 European Pat. Off. .
721129 1/1996 European Pat. Off. .
41 19024 12/1992 Germany .

OTHER PUBLICATIONS

PCT/EP98/01351, "International Search Report—Information on Patent Family Members," Sep. 8, 1998, pp. 1–3.

*Primary Examiner*—David M. Shay
*Attorney, Agent, or Firm*—Akin, Gump, Strauss, Hauer & Feld, L.L.P.

[57] ABSTRACT

A technique and apparatus are provided for simulating a laser treatment on the eye by pretreating a contact lens. A proposed laser treatment is developed using a patient's eye data. That laser treatment is then performed by an excimer laser system onto a contact lens blank. The lens blank is then placed on the patient's eye and the patient's resulting visual acuity are measured. If within acceptable limits, the treatment is then performed on the patient's eye. Otherwise, the treatment pattern is adjusted and the either original lens profiled with the difference or a new lens profiled with the new treatment pattern. This is repeated until the error falls within acceptable limits. Alternatively, spectacle lenses can be used instead of contact lenses.

29 Claims, 3 Drawing Sheets

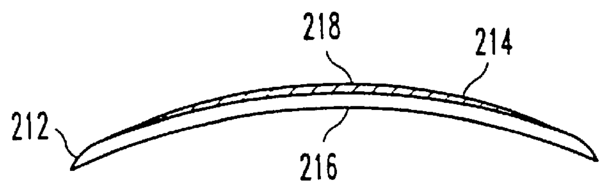
Fig.1A
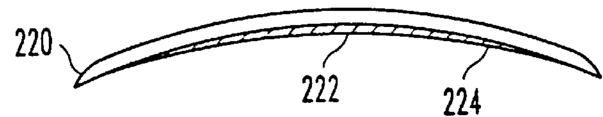
Fig.1B
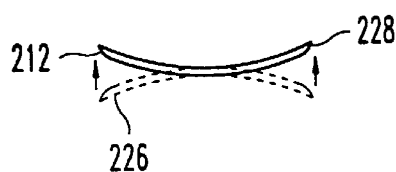
Fig.1C
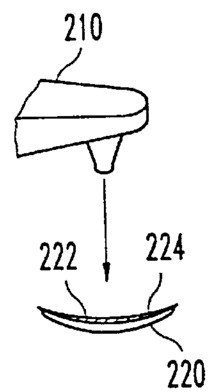
Fig.3
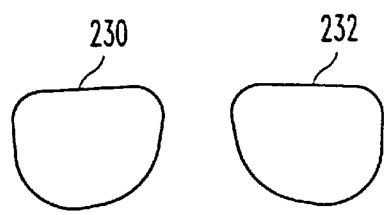
Fig.4A
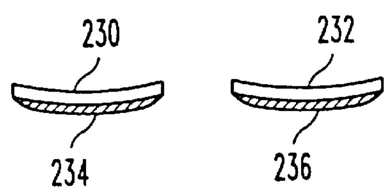
Fig.4B
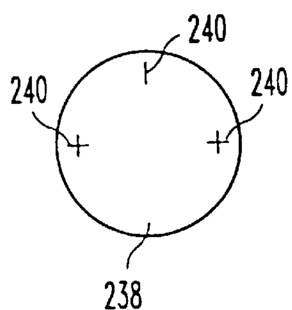
Fig.5
244
Fig.6B
242
Fig.6A

SIMULATING A LASER TREATMENT ON THE EYE BY PRETREATING A CONTACT LENS

BACKGROUND OF THE INVENTION

1. Field of the Invention

The invention generally relates to vision correction through laser treatment of the eye, and more specifically to a method of pretesting a laser treatment by first performing the treatment on a contact lens that is then worn by the patient.

2. Description of the Related Art

The field of corrective eye surgery has seen remarkable advances over the past two decades. Eye surgeons have sought and developed solutions for vision correction more permanent than prosthetic devices such as glasses and contact lenses. The initial surgical techniques employed RK, or radial keratotomy, in which the surgeon used a blade to make incisions in the eye, causing the cornea to flatten or steepen in desired directions. This procedure has been largely supplanted by the use lasers, especially excimer lasers, to actually shape the cornea in a technique known as PRK, or photo-refractive keratectomy. This technique literally resculpts the cornea of the eye using an excimer, "cold light" laser that removes material without significantly heating stromal tissue. A variety of techniques have been developed using these lasers, including scanning technologies, fixed and variable spot size technologies, erodible mask technologies, and the ablation of the subsurface of the cornea in a technique known as LASIK, or laser in situ keratomileusis. Some of these techniques and systems for practicing them are further described in U.S. patent application Ser. No. 08/324,782, filed Oct. 18, 1994, entitled "Excimer Laser System for Correction of Vision with Reduced Thermal Effects"; U.S. patent application Ser. No. 08/338,495, filed Nov. 15, 1994, entitled "Apparatus for Modifying the Surface of the Eye Through Large Beam Laser Polishing and Method of Controlling the Apparatus"; and U.S. Pat. No. 4,840,175 to Peyman, issued Jun. 20, 1989, entitled "Method for Modifying Corneal Curvature," all of which are hereby incorporated by reference.

All of these systems, however, demand precision—although follow-up surgeries can be performed, once the tissue is removed, it is permanently removed. Therefore, it is highly desirable that a treatment pattern developed for one of these systems be accurate. To this end, a technique would be desirable for pretesting a treatment pattern before actually performing that treatment pattern on the patient's eye.

SUMMARY OF THE INVENTION

According to the invention, a laser treatment pattern is pretested before actually being performed on the patient's eye. A proposed treatment pattern is developed based on the patient's vision, eye topography, or other criteria, and then a contact lens blank is provided that reacts to laser treatment similarly to how the patient's eye will react to that treatment. The contact lens is placed under the laser system and ablated or otherwise eroded by the laser according to the proposed treatment pattern. The lens is then placed on the patient's eye, and the effect of the treatment pattern is assessed.

Many permutations of this technique are possible. Either the concave or convex surface of the lens can be ablated, and either the treated surface or the untreated surface can be placed against the patient's eye. Preferably, the treated surface is placed against the patient's eye, so that a topography system can then assess the curvature of the lens as it sits on the patient's eye. The lens can be weighted to allow for asymmetric or aspherical treatment patterns, such as for astigmatism or other irregular shapes. Further, the power of the laser system can be adjusted so that the resulting refractive effect on the lens blank corresponds to the refractive effect that will occur when the patient's cornea is treated. Instead of a contact lens, the treatment pattern can be diverged, for example, onto spectacle lens blanks. Marks can be placed on either the contact lens blank or the spectacle lens blank to assure proper alignment within the excimer system. Preferably, an excimer laser system is used.

If the visual results of the treatment on the contact lens are suitable, the treatment is then performed on the patient's eye, such as through PRK (photo refractive keratectomy) or through LASIK (laser in situ keratomileusis). If the results are not acceptable, the proposed treatment pattern is modified based on the patient's resulting visual acuity and topography. Then, either a new lens blank is treated, or the existing pretreated lens blank is further treated with the difference between the original treatment pattern and the new treatment pattern. This process is repeated until the patient's resulting vision falls within acceptable limits.

BRIEF DESCRIPTION OF THE DRAWINGS

A better understanding of the present invention can be obtained when the following detailed description of the preferred embodiment is considered in conjunction with the following drawings, in which:

FIG. 3 is an alternative technique for creating a pretreatment contact lens according to the invention;

FIGS. 4A and 4B are illustrations of spectacle lenses alternatively created and used according to the invention;

FIG. 5 is an illustration of details of a contact lens for use with the technique according to the invention; and FIGS. 6A and 6B are alternative contact lens blank profiles for use in the technique according to the invention.

DETAILED DESCRIPTION OF THE PREFERRED EMBODIMENT

Figure 1:
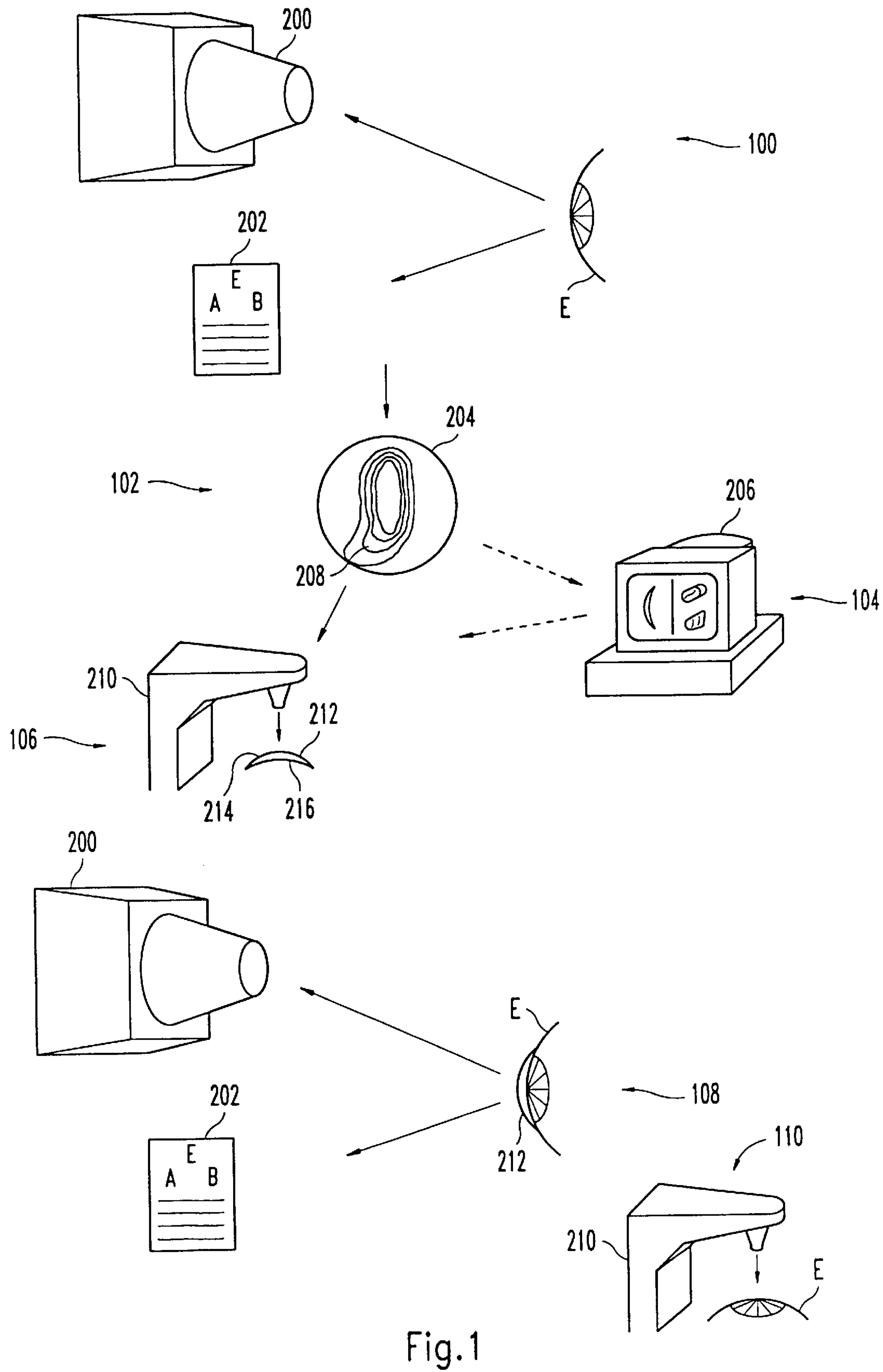
FIG. 1 is a diagram illustrating the steps of creating a pretreatment contact lens and using that lens according to the invention.

Turning to the drawings, FIG. 1 illustrates steps of the technique according to the invention for pretesting a laser treatment pattern for vision correction. Beginning at a step 100, the vision of a patient's eye E is tested with a variety of methods, including a topographic system 200 and a visual acuity test through an eye chart 202. The actual testing methods can vary, but in general, an ophthalmologist will typically obtain vision data including the dioptric degree of correction necessary, a cylinder axis of an astigmatism, and a dioptric degree of astigmatism. Further, using advanced eye topography systems, such as the topography system 200, a topographic profile of the eye is developed and provided as data. This topographic profile shows irregular astigmatism and other irregularities in the cornea of the eye. An exemplary topography system would be the System 2000 available from EyeSys, Inc., of Houston, Tex.

This testing yields eye profile data 204 in a step 102. This profile data 204 will typically include a topographic map of the irregularities of the surface of the eye, along with a degree of overall dioptric correction necessary, such as −5.00 diopters. Based on this data, ophthalmologists, on their own or through a service, develop treatment profiles for correcting the vision of the eye E in a step 104. The treatment profile developed typically depends on the type of eye surgery that is going to be performed and with what type of laser surgery system. A simple profile may correct for a certain degree of myopia, with no irregularities being corrected and no astigmatic correction. A more complex profile may remove an irregular astigmatism from the eye E surface along with providing an overall correction for myopia or hyperopia.

The types of treatment developed can be wide ranging. Many systems and techniques for laser surgery are available, including variable spot size constantly centered systems, fixed spot size scanned systems, or variable spot size scanned systems, along with a wide variety of other types of systems. Preferably, a treatment profile is developed for a Keracor® 117 or Keracor® 217 excimer laser eye surgery system. These systems, sold by Chiron Technolas GmbH of Munich, Germany, use a "plano scan" technique described in U.S. patent application Ser. No. 08/324,782, which is hereby incorporated by reference.

Further, a distributed system can be used for developing the profile in step 104. For example, the data 204 can be transmitted to a remote computer 206, such as over a network or via disk, where a doctor or technician develops a treatment profile. This technique is described in U.S. patent application Ser. No. 08/656,855, filed May 30, 1996, to Kristian Hohla, entitled "Distributed Excimer Laser Surgery System," which is hereby incorporated by reference. On this remote system 206, a treatment pattern for correction of an irregular astigmatism, illustrated as an astigmatism 208 of the data 204, is developed, along with a pattern for the degree of overall dioptric correction necessary. Alternatively, this treatment pattern can be developed in a laser system 210 itself, where the laser system is a Keracor® 217, for example.

In any case, however the treatment pattern is developed, it is then implemented in the laser system 210 in a step 106. In this step, a contact lens 212 is placed at the focal path of the disclosed excimer laser system 210, and the treatment is performed on the contact lens 212. This contact lens 212 can be of a variety of materials, such as a polymer. An example is Etafilcon A used in Acuvue Contact Lenses from Johnson & Johnson. The material can be flexible or rigid, and can have a similar ablation characteristic to that of the cornea of the eye E resulting in a similar degree of refractive correction when the treatment pattern of the laser system 210 is applied. Alternatively, it can have a different rate of ablation relative to the cornea of the eye E and the laser system 210 power or shot count adjusted by a corresponding percentage such that the ultimate refractive change on the lens 212 equals that which would be experienced by the cornea of the eye E. As shown in step 106, a convex surface 214 of the lens 212 is ablated. Alternatively, a concave surface 216 could instead be ablated. This is further described below in conjunction with FIGS. 1B and 3. Referring to FIGS. 1A and 1B, in FIG. 1A the lens 212 is shown with an area 218 removed from the convex surface 214. Alternatively, in FIG. 1B, shown is a lens 220 with an area 222 removed from a concave surface 224, similar to the concave surface 216. FIG. 1C further illustrates how the lens 212 (or alternately the lens 220) can be inverted from an original position 226 to an inverted position 228. Thus, the concave or the convex side of the lens can be ablated, and in either case can be reversed by inverting the lens from a first position to a second position, such that the concave surface becomes a convex surface, and vice versa, as illustrated in FIG. 1C.

Turning to a step 108, the lens 212 is placed on the patient's eye E with the treated convex surface 214 towards the eye E after the "inversion" of FIG. 1C, and then the topography system 200 and the eye chart 202, or other devices, are used to determine the resulting degree of correction and visual acuity. In this step 108, if the lens 212 is made of a thin, flexible material, and preferably if the ablated portion of lens 212 is placed towards the eye E, such as by inverting the lens as illustrated in FIG. 1C, then the topography system 200 can, to some extent, predict the final topography of the eye E after it is treated. In any case, other visual acuity measurement techniques, such as the eye chart 202, are used to determine the visual acuity resulting from the treatment.

If the visual acuity is determined to be acceptable, then in a step 110 the laser surgery system 210 treats the eye E using the treatment pattern developed in steps 100–108. If at step 108 the visual acuity is not acceptable, modifications may be made to the treatment pattern developed in step 104, and the lens 214 or a new lens is ablated with the new treatment pattern. If a new lens is used, the new treatment pattern is used. If the original lens 214 is used, then the differences between the original and the new treatment pattern are ablated into the lens 214. Further, referring below to FIG. 5, it will be appreciated that if an aspheric treatment pattern is used, the lens 214 should first be oriented in its original orientation before being ablated with the difference between the original and the new treatment pattern (or at least the laser system 210 made aware of the orientation of the lens).

Figure 2:
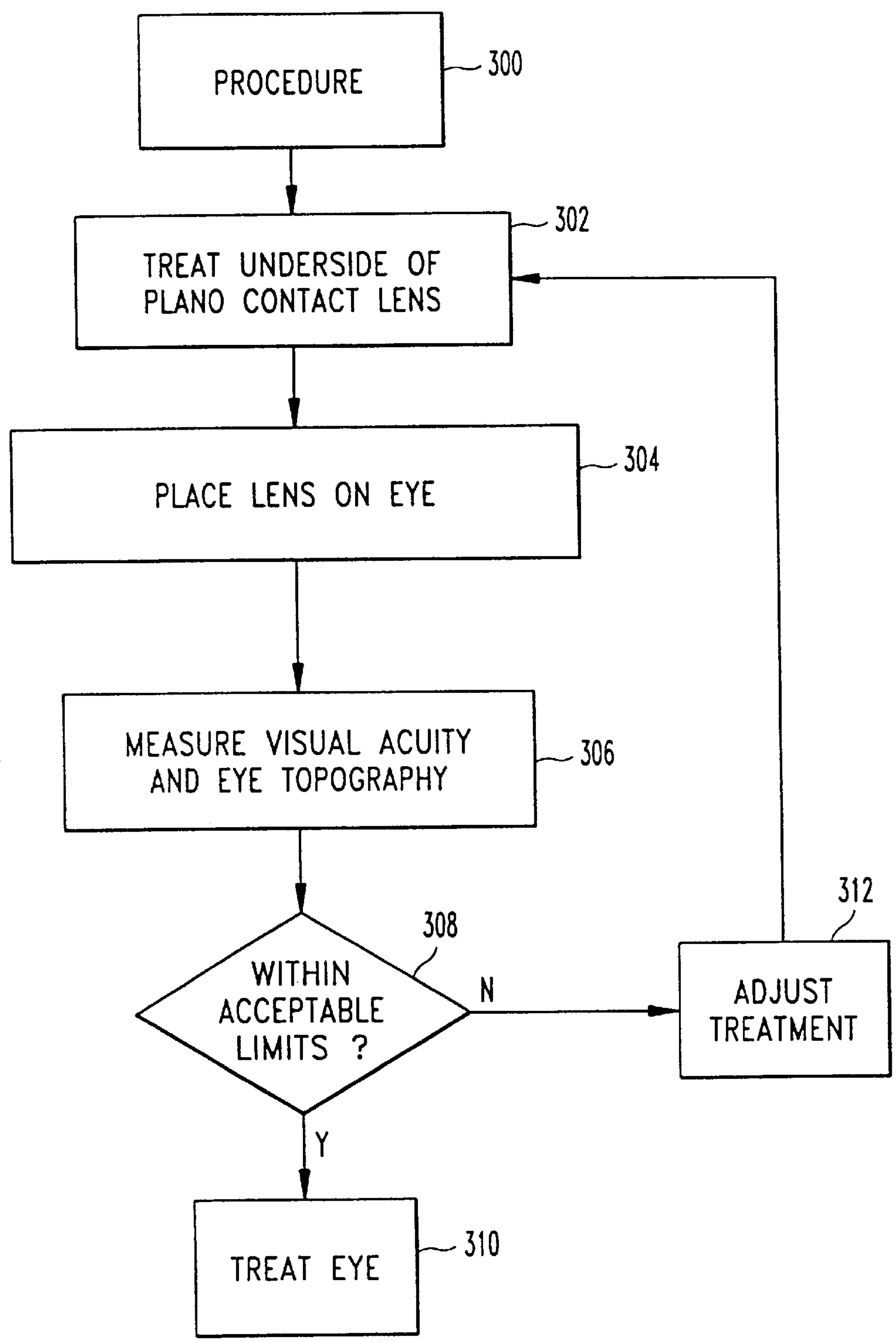
FIG. 2 is a flowchart illustration of the steps for pretesting a laser treatment according to the invention.

Turning to FIG. 2, shown is a flowchart illustration of the pretesting according to the invention. The procedure begins at step 300, where a procedure for appropriate vision correction is generated. Proceeding to step 302, the underside of a plano (i.e., zero refractive correction) contact lens is treated with the excimer laser surgery system 210 for appropriate vision correction. If the underside is treated, and the underside is to be placed towards the eye, actually a mirror image of the ultimately desired treatment pattern must be applied to the underside of the contact lens 214.

Proceeding to step 304, the lens 214 is placed on the eye, and then at step 306, visual acuity and topography are measured. Proceeding to step 308, it is determined whether the visual acuity is within acceptable limits. If so, control proceeds to 310 where the eye E is treated. If not, control proceeds to step 312, where the treatment is adjusted accordingly, and control proceeds to step 302.

Turning to FIG. 3, as previously discussed, shown is an alternative to step 106 of FIG. 1. In FIG. 3, the excimer laser system 210 ablates the concave surface 224 of the contact lens 220, removing material 222. This contact lens 220 could then be placed against the eye E, either with the treated surface 224 towards the eye or, after "inverting" as illustrated in FIG. 1C, away from the eye E.

Excimer lasers generally form slight ridges in the surface that is treated. Therefore, the surface of the lens 212 or 220 could be slightly "rough" and cause visual distortions, especially to the topography system 200. For this reason, the treated surface 216 or 224 is preferably placed towards the eye E, so that the liquid surface on the eye E fills in these ridges, reducing their optical effect. Conceivably, if worn for long periods, the lens might irritate the eye E. But for a short amount of time, the irritation will be minimal.

Turning to FIGS. 4A and 4B shown are lenses for spectacles 230 and 232. These lenses can be used as an alternative to the contact lenses 220 or 212. In this case, the material is removed from the spectacle lenses 230 and 232, yielding a removed area 234 and 236. Referring back to FIG. 3 and step 106 of FIG. 1, it will be appreciated that to form an appropriate correction on the lenses 230 and 232, the treatment pattern must be expanded through some optical technique or through computer control. In any case, these lenses 230 and 232 can alternatively be used to pretest the treatment. In this case, the lenses are preferably made of a clear, hard material, such as PMMA.

Turning to FIG. 5, certain details of the contact lens 212 or 220 are illustrated. A weight 238 is shown, which orients the contact lens 212 or 220 properly in the eye should an aspheric treatment pattern be used. Further, shown are markings 240, which are used to appropriately align the contact lens 212 or 220 or the spectacle lenses 230 and 232 when placed under the laser system 210.

With regard to proper alignment, the contact lens 212 or 220 can be placed on the patient's eye E before the treatment is performed on the contact lens 212 or 220. This reduces misalignment, because the patient would be asked to focus on an eye fixation point, and the treatment will thus be self-aligning, because the alignment would be the same as if the contact lens 212 or 220 were absent. This technique could be used either with or without inverting the lens before performing the visual acuity/topography testing.

Finally, turning to FIGS. 6A and 6B, alternatives are shown for the contact lens blank 212 or 220 used according to the invention. A first blank 242 is shown which is a piano contact lens; that is, it provides no correction or change of refractive power when placed on the eye. Any correction or refractive power would be imparted during the treatment of step 106. In FIG. 6B, a contact lens 244 with an initial dioptric correction is shown. Perhaps it is known that a certain treatment will result in a certain degree of dioptric correction overall. So, for example, the lens 244 may be precorrected by +5.00 diopters, for example. Then, only the differences in the treatment pattern that are in addition to a +5.00 diopter of treatment are imparted during the treatment step 210. This could result in a faster removal of material from the lens when the principal effect desired to be studied is the asymmetric astigmatism 208, for example.

Preferably, the excimer laser system 210 includes a "pretreatment mode" for ablating the spectacle lens 230 or 232 or the contact lens 212 or 220. In this "pretreatment mode," the laser system 210 adjusts for the type and ablation rate of material used in the lens, for the fact that a mirror image of the treatment pattern might be needed, for the fact that the spectacle lens 230 or 232 have a larger area to be treated, and for the fact that this treatment may be the difference between an earlier calculated treatment and the present calculated treatment. Preferably, the pretreatment mode of the laser system 210 includes some combination of these options for greater flexibility and the choice of materials, type of lenses, and changes in treatment patterns. For example, if the material of the contact lens 212 is a Hema Lens made from a polymer of methacryl-acid, it may have a different rate of ablation than corneal tissue. Thus, when placed in "pretreatment mode," the excimer laser system 210 either increases its power per shot or provides for a greater number of shots for each equivalent shot in the treatment pattern. The pretreatment mode can even include a user input for the type of material of the lens, and automatically calculate the corresponding ablation rate to appropriately pretreat the lens. The pretreatment mode can further include specifications of the orientation of the lens if an aspheric or an asymmetrical type of treatment pattern is to be used. In this case, an alignment beam of the excimer laser system 210 could be used, for example, to designate the position of the markers 240, and the excimer laser system 210 could adjust the corresponding angle of the treatment pattern based on the angle of the lens 212 specified by those alignment markers. A variety of other options for the pretreatment mode will become apparent to one with an understanding of the system and techniques according to the invention.

To summarize, a laser system, such as an excimer laser system 210, is used to pretreat a contact lens or a spectacle lens, and then that lens is placed on or in conjunction with the eye The visual acuity resulting from that treatment is measured, and if appropriate, the eye is treated. Otherwise, alterations are made in the treatment pattern, and the eye again tested until an appropriate treatment is derived.

The foregoing disclosure and description of the invention are illustrative and explanatory thereof, and various changes in the details of the illustrated apparatus and construction and method of operation may be made without departing from the spirit of the invention.

What is claimed is:

1. A laser system for sculpting of the eye, the laser system comprising:

a laser for treatment of corneal tissue;

an optical system for directing the laser;

a control system coupled to the laser and the optical system, the control system having a pretreatment mode for sculpting a test lens to be applied to a patient's eye before the patient's eye is treated by the laser system.

2. The system of claim 1, wherein the pretreatment mode includes an option to select from a variety of lens materials.

3. The system of claim 1, wherein the pretreatment mode includes an option to specify the orientation of the lens under the laser system.

4. The system of claim 1, wherein the pretreatment mode includes an option to specify that the mirror image of an ultimate treatment pattern is to be imparted onto the lens surface.

5. The system of claim 1, wherein the pretreatment mode includes an option to expand the treatment pattern for a spectacle lens.

6. The system of claim 1, wherein the pretreatment mode includes an option to specify that the difference between a previous treatment onto a lens and the present treatment onto the lens is to be imparted onto the lens.

7. A method of pretesting the effect of a laser treatment pattern on the eye, the method comprising the steps of:

a) providing a contact lens blank suitable for laser shaping;

b) performing a laser treatment on the contact lens so that the contact lens assumes a corrective profile corresponding to the laser treatment pattern;

c) placing the contact lens on the eye of a patient; and d) measuring the patient's vision with the laser treated contact lens on the eye.

8. The method of claim 7, wherein said step (b) further comprises the steps of:

i) providing a laser system; and ii) adjusting the laser system power so that the corrective profile formed on the contact lens after the laser treatment is equal in refractive power to a corresponding treatment on an eye.

9. The method of claim 7, wherein said step (a) further comprises the step of providing a contact lens blank that optically responds to the laser treatment of step (b) as does the tissue of an eye.

10. The method of claim 7, wherein step (a) further comprises the step of providing a weighted contact lens, and wherein step (b) further comprises the step of performing an aspheric treatment pattern.

11. The method of claim 7, wherein step (a) further comprises the step of providing a plano contact lens blank.

12. The method of claim 7, wherein said step d) further comprises the steps of:

i) measuring the patient's visual acuity; and ii) profiling the topography of the treated contact lens on the eye.

13. The method of claim 7, wherein step (c) is performed before step (b).

14. The method of claim 7, wherein step (c) is performed after step (b).

15. The method of claim 7, wherein said step (b) further comprises performing an excimer laser treatment.

16. The method of claim 7 further comprising the step of:

e) after step (d), performing the laser treatment on the eye.

17. The method of claim 16, wherein step (e) further comprises the step of performing in situ keratomileusis.

18. The method of claim 7, wherein the contact lens blank includes an initial convex, surface and an initial concave surface, wherein said step (b) further comprises the step of performing a laser treatment on the initial convex surface of the contact lens to form a treated surface.

19. The method of claim 18, wherein said step (c) further comprises the step of placing the contact lens on the eye of a patient with the treated surface away from the eye.

20. The method of claim 18 wherein said step (c) further comprises the steps of:

i) reversing the lens so that the treated surface is then a concave surface; an ii) placing the lens on the eye of a patient with the treated surface towards the eye.

21. The method of claim 7, wherein the contact lens blank includes an initial convex surface and an initial concave surface, and wherein said step (b) further comprises the step of performing a laser treatment on the initial concave surface of the contact lens to form a treated surface.

22. The method of claim 21, wherein said step (c) further comprises the step placing the contact lens on the eye of a patient with the treated surface towards the eye.

23. The method of claim 21, wherein said step (c) further comprises the steps of:

i) reversing the lens so that the treated surface is then a convex surface; and ii) placing the lens on the eye of a patient with the treated surface away from the eye.

24. The method of claim 1 further comprising the steps of:

e) determining an error factor in said measuring step;

f) modifying the laser treatment pattern in response to the determined error factor; and g) repeating steps (a)–(d).

25. The method of claim 24, wherein in said step (g), the same contact lens blank is provided in repeated step (a) as in original step (a), and wherein the laser treatment of repeated step (b) performs as the laser treatment only differences between the original laser treatment pattern and the modified laser treatment pattern.

26. The method of claim 24, further comprising the steps of:

h) repeating steps (a)–(g) until the error factor is below an acceptable threshold; and i) after step (h), performing the laser treatment on the eye.

27. The method of claim 26, wherein step (i) further comprises the step of performing in situ keratomileusis.

28. A method of pretesting the effect of a laser treatment pattern on the eye, the method comprising the steps of:

a) providing a specticle lens blank suitable for laser shaping;

b) performing a laser treatment on the spectacle lens so that the spectacle lens assumes a corrective profile corresponding to the laser treatment pattern;

c) placing the lens in visual alignment with the eye of a patient; and d) measuring the patient's vision with the laser treated spectacle lens in visual alignment with the eye.

29. The method of claim 22, wherein the step of providing a lens blank further comprises the step of providing a spectacle lens blank.

* * * * *

UNITED STATES PATENT AND TRADEMARK OFFICE

CERTIFICATE OF CORRECTION

PATENT NO. : 5,941,874
DATED : August 24, 1999
INVENTOR(S) : Kristian Hohla

It is certified that error appears in the above-identified patent and that said Letters Patent is hereby corrected as shown below:

Column 7,
Line 22, delete the "," after the word "convex".

Column 8,
Line 8, change "claim 1" to -- claim 7 --.
Line 38, change "claim 22" to -- claim 28 --.

Signed and Sealed this

Sixth Day of November, 2001

*Attest:*

Nicholas P. Godici

NICHOLAS P. GODICI

*Attesting Officer* *Acting Director of the United States Patent and Trademark Office*